US00PP18522P3

(12) United States Plant Patent
Olesen

(10) Patent No.: US PP18,522 P3
(45) Date of Patent: Feb. 26, 2008

(54) MINIATURE ROSE PLANT NAMED 'POULPAR042'

(50) Latin Name: ***Rosa* hybrid**
Varietal Denomination: Poulpar042

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 152 days.

(21) Appl. No.: 11/360,915

(22) Filed: Feb. 22, 2006

(65) Prior Publication Data

US 2007/0199113 P1 Aug. 23, 2007

(51) Int. Cl.
*A01H 5/00* (2006.01)

(52) U.S. Cl. ..... Plt./121

(58) Field of Classification Search ..... Plt./121
See application file for complete search history.

*Primary Examiner*—Annette H Para

(57) ABSTRACT

A new miniature rose plant that has abundant, pink flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar042'.

SUMMARY OF THE INVENTION

The present invention constitutes a new and distinct variety of miniature rose plant which originated from a controlled crossing between the female seed parent, an unnamed seedling, and the male pollen parent 'Korstoffein', U.S. Plant Pat. No. 11,242.

The two parents were crossed during the summer of 2002 and the resulting seeds were planted in a controlled environment in Fredensborg, Denmark. The new variety, named 'Poulpar042', originated as a single seedling from the stated cross.

The new variety may be distinguished from its female seed parent primarily by flower color. The seed parent variety has red flowers, while 'Poulpar042' has light pink flowers.

The new variety may be distinguished from its male pollen parent by the following combination of characteristics:

1. The pollen parent has 25 to 30 petals. 'Poulpar042' has 70 petals, 10 to 15 of which are petaloids.
2. Flower petals of the pollen parent are Yellow-Orange 19D while flower petals of the claimed plant are Red-Purple Group 62D.

The objective of the hybridization of this rose variety for commercial culture was to create a new and distinct variety with unique qualities, such as:

1. Uniform and abundant light pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'Poulpar042' from all other varieties of which we are aware.

As part of the rose development program, Mogens Nyegaard Olesen germinated the seeds from the aforementioned hybridization and conducted evaluations on the resulting seedlings in a controlled environment in Fredensborg, Denmark. 'Poulpar042' was selected by the inventor as a single plant from the progeny of the hybridization in 2003.

Asexual reproduction of 'Poulpar042' by cuttings and traditional budding was first done by Mogens Nyegaard Olesen in the nursery in Fredensborg, Denmark in April 2003. This initial and other subsequent propagations conducted in controlled environments have demonstrated that the characteristics of 'Poulpar042' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar042'. Specifically illustrated in the drawing:

FIG. 1.1; Cluster of flower buds at various stages of development;

FIG. 1.2; Open flowers;

FIG. 1.3; Sepals, receptacle, and pedicel;

FIG. 1.4; Flower petals, detached;

FIG. 1.5; Juvenile growth;

FIG. 1.6; Mature leaves; and

FIG. 1.7; Bare stem.

DETAILED DESCRIPTION OF THE VARIETY

The following is a description of 'Poulpar042', as observed in its growth in a glasshouse in Fredensborg, Denmark. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulra018', U.S. Plant Pat. No. 15,405, are compared to 'Poulpar042' in Chart 1.

CHART 1

| | 'Poulpar042' | 'Poulra018' |
|---|---|---|
| Petalage: | 70 petals, 10 to 15 of which are petaloids | 30 to 34 petals, with 4 to 6 petaloids |
| Flower Diameter: | 50 to 60 mrn. | 35 mm |
| General Tonality of Flower Color: | Red Group 52D to 56C with intonations of Red Group 49A | Red 49C |

FLOWER AND FLOWER BUD

Blooming habit: Continuous.

Flower bud:

*Size.*—Upon opening, 24 to 27 mm in length from base of receptacle to end of bud. Bud diameter is normally 10 mm.

*Bud form.*—Pointed ovate.

*Bud color.*—As sepals unfold, petals are Red Group 38C to 49B.

*Sepals.*—Upper Surface: Color: Green Group 138A to 138B with anthocyanic pigments of Greyed-Purple Group 183A at the apex. Texture: Strong pubescence observed. Lower Surface: Color: Yellow-Green Group 146A with occasional anthocyanic pigments of Greyed-Purple Group 183A at the apex. Texture: Smooth with light pubescence. Shape: Apex: Cirrhose. Base: Flat at union with receptacle. Margins: Margins have strong foliaceous appendages on three of the five sepals. Stipitate glands are sparse. Size: 25 mm long by 5 mm wide.

*Receptacle.*—Surface Texture: Smooth and lightly pubescent. Shape: Pear shaped. Size: 7 mm (h)×6 mm (w). Color: Yellow-Green Group 144A. Anthocyanin: None observed.

*Pedicel.*—Surface: Smooth. Length: 25 to 27 mm average length. Diameter: Average 3 mm. Color: Yellow-Green Group 144A. Strength: Medium strength.

*Borne.*—Flowers are borne singularly or in small clusters of 3 buds per flowering stem on average.

Flower bloom:

*Fragrance.*—Light floral scent.

*Duration.*—As a pot plant, flowers last up to 28 days. After flowers have fully matured, petals do not fall cleanly away from plant.

*Size.*—50 to 60 mm in diameter. Average flower depth is 18 to 23 mm.

*Form.*—General shape is cupped when flowers are opening. As flowers fully mature, form resembles a rosette with many petals packed tightly into quarter section.

*Shape of flower, side view.*—Upon opening: The upper portion is flat. The lower portion is flat. After opening: The upper portion is flat. The lower is concave.

Petalage: Normally 70 petals, 10 to 15 of which are petaloids.

Color:

*Upon opening, petals.*—Outermost petals: Upper Surface: Red Group 56D. Lower Surface: Red Group 56B to 56C. Innermost petals: Upper Surface: Red Group 56D. Lower Surface: Red Group 56B to 56C. Outermost petal, basal petal spots upon opening: Upper surface: Yellow-Green Group 150D. Lower surface: Yellow-Green Group 150D. Innermost petal, basal spots upon opening: Upper surface: Yellow Group 8C to 8D. Lower surface: Yellow-Green Group 150D.

*After opening, petals.*—Outermost petals: Upper Surface: Red-Purple Group 62D. Lower Surface: Red Group 56A. Innermost petals: Upper Surface: Red-Purple Group 62D. Lower Surface: Red Group 56A. Basal petal spots after opening: Upper surface: Green-White Group 157B. Lower surface: Green-White Group 175B.

General tonality: On open flower Red Group 52D to 56C with intonations of Red Group 49A. No change in tonality at the end of the $10^{th}$ day.

Petals:

*Petal reflex.*—Strong reflex at margins.

*Petal margin.*—Entire with slight point at the center. Weak undulation of margins observed.

*Shape.*—General narrow elliptical. Base: Acute. Apex: Rounded.

*Size.*—Petal size varies. Outer petals are 30 mm (l)×26 mm (w). Inner petals are 20 mm (l)×15 mm (w).

*Texture.*—Smooth.

*Thickness.*—Somewhat thin.

Petaloids:

*Quantity.*—10 to 15 on average.

*Size.*—15 mm long×8 mm wide.

*Shape.*—Irregular narrow elliptical.

*Color.*—Upper petaloid surface is Red-Purple Group 62D. The lower surface is Red Group 56A. Basal petal spots on petaloids are Green-White Group 157B on upper and undersurfaces.

Reproductive organs:

*Pollen.*—None observed.

*Anthers.*—Size: 2 mm long. Color: Yellow Group 4D and Yellow-Orange Group 15A. Quantity: 45 to 50.

*Filaments.*—Color: Yellow Group 5C. Length: 4 to 5 mm.

*Pistils.*—Length: Average 7 mm. Quantity: 40 to 45.

*Stigmas.*—Slightly inferior in relative to the length of the filaments and the height of the anthers. Color: White Group 155A.

*Styles.*—Color: Red Group 53B.

*Seed formation.*—Not observed.

PLANT

Plant growth: Moderate upright to bushy. Very compact. When grown as an 10.5 cm pot plant on its own roots, the average height of the plant itself is 17 to 20 cm and the average width is 18 cm.

Stems:

*Color.*—Young wood: Yellow-Green Group 144C. Older wood: Yellow-Green Group 144A.

*Internodal distance.*—On mature canes, 17 to 20 mm.

*Length of stems.*—On average, canes are 10 to 13 cm from the base of the stem to the flowering portion.

*Diameter.*—Normally 3 mm.

*Surface texture.*—Young wood: Smooth. Older wood: Smooth.

Prickles:

*Incidence.*—4 prickles per 10 cm of stem.

*Length.*—Average 4 mm.

*Shape.*—Upper side: Flat. Lower side: Flat.

*Color.*—Young wood: Greyed-Red Group 181B. Mature wood: Greyed-Red Group 181B.

Plant foliage: Normal number of leaflets on normal leaves in middle of the stem is 5 to 7 leaflets.

*Compound leaf size.*—Normally 70 to 75 mm (l)×50 to 65 mm (w).

*Quantity.*—5 leaves per 10 cm of stem.

*Color.*—Juvenile foliage: Upper Leaf Surface: Yellow-Green Group 144A to 145A. Anthocyanic intonations of Greyed-Red Group 181A on the margins. Lower Leaf Surface: Yellow-Green Group 146A to 145A. Mature foliage: Upper Leaf Surface: Yellow-Green Group 147A to 146A. Occasionally margins have anthocyanic pigments of Greyed-Red Group 178A. Lower Leaf Surface: Yellow-Green Group 147B.

Plant leaves and leaflets:

*Stipules.*—Size: 6 mm in length. Shape: Linear, slightly broad based with outward extending apecies. Margins: Finely serrated with few stipitate glands. Color: Yellow-Green Group 144A.

*Petiole.*—Length: 10 to 13 mm. Diameter: Normally 1 mm. Upper surface: Color: Yellow-Green Group 146B. Observations: Few stipitate glands. Lower surface: Color: Yellow-Green Group 144B. Observations: Few small prickles observed.

*Rachis.*—Size: 20 to 24 mm in length. Upper surface: Color: Yellow-Green Group 146B with anthocyanic pigments of Greyed-Orange Group 175A. Observations: Few stipitate glands. Lower surface: Color: Yellow-Green Group 144B. Observations: Few small prickles observed.

*Leaflet.*—Size: 38 mm in length by 42 mm wide. Edge: Serrated. General Shape: Ovate. Apex Shape: Acute. Base Shape: Rounded to cordate. Texture: Smooth. Thickness: Average. Arrangement: Odd pinnate. Venation: Reticulate. Leaf Gloss: Matte finish.

Disease resistance: Average resistance to powdery and downy mildew, black spot, and *Botrytis* under normal growing conditions in Odense, Denmark.

It is claimed:

1. A new and distinct variety of rose plant of the miniature class named 'Poulpar042', substantially as illustrated and described herein, due to its abundant, pink flowers, vigorous growth, compact habit, suitability for production from softwood cuttings in pots, and durable flowers and foliage that make the variety suitable for distribution in the floral industry.

* * * * *

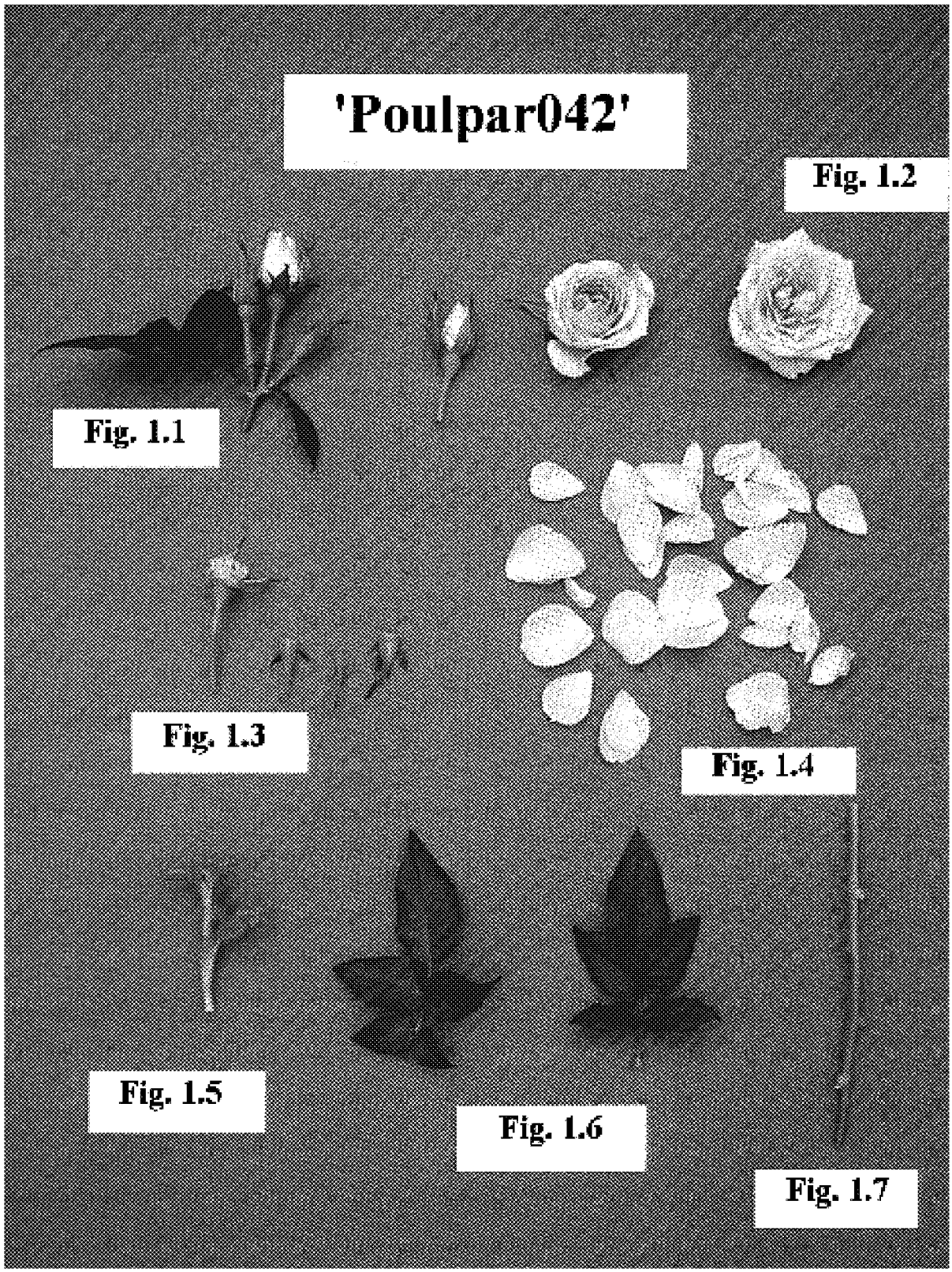
'Poulpar042'
Fig. 1.2
Fig. 1.1
Fig. 1.3
Fig. 1.4
Fig. 1.5
Fig. 1.6
Fig. 1.7